July 8, 1969 H. R. SPOTO, SR Plant Pat. 2,901
PEACH TREE
Filed Dec. 15, 1967
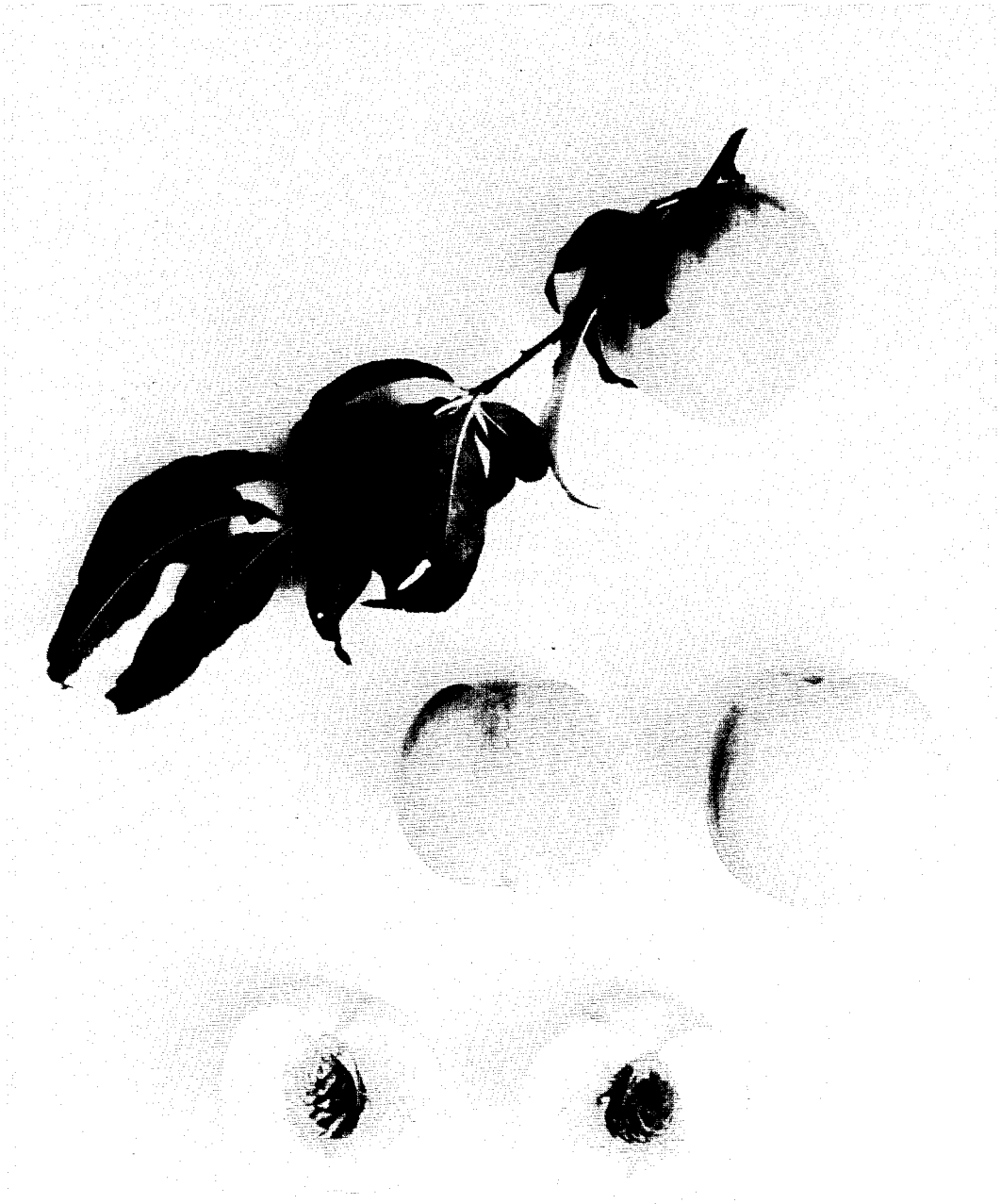
INVENTOR
Henry R. Spoto, Sr.
BY Webster & Webster
ATTORNEYS

United States Patent Office

Plant Pat. 2,901
Patented July 8, 1969

2,901
PEACH TREE

Henry R. Spoto, Sr., 790 N. Township Road,
Yuba City, Calif. 95991

Filed Dec. 15, 1967, Ser. No. 691,075
Int. Cl. A01h 5/08
U.S. Cl. Plt.—43 1 Claim

ABSTRACT OF THE DISCLOSURE

A peach tree which is large in size, hardy and vigorous in growth, spreading and round-topped in form, and a regular and productive bearer of large, late ripening freestone fruit having yellow flesh, and yellow skin substantially overspread with red at maturity.

*Origin of the variety*

I planted a seed of an unknown variety of freestone peach on my ranch located near Yuba City, Sutter County, Calif., and the resultant seedling—which was maintained under cultivation and close observation during the period of its growth—evidenced, when it came into bearing, that it was a new and distinct variety by reason of certain characteristics as will hereinafter appear.

*Asexual reproduction of the variety*

Upon recognition by me of the novelty of the variety, I asexually reproduced it by budding on seedlings of the Lovell peach (unpatented) in an orchard on my ranch located as aforesaid. These reproductions ran true to the original tree in all respects.

*Summary of the variety*

The present new and distinct variety of peach tree is large in size, hardy and vigorous in growth, spreading and round-topped in form, and a regular and productive bearer of large freestone fruit having yellow flesh, and yellow skin substantially overspread with red at maturity; such fruit having firm flesh, and a late ripening period. In a normal year the fruit ripens, for harvest, about September 7th; this ripening period being a few days before the Kirkman Gem (United States Plant Patent No. 506).

*Brief description of the drawing*

The drawing is an illustration, by photographic reproduction in color, of a twig with leaves and a fruit remaining attached; other fruit being shown detached, and one such detached fruit being cut in half to expose the flesh, and with the stone remaining in one cut half.

*Description of the variety*

The potanical details of this new and distinct variety of peach tree—with color definitions (except those in common color terms) referenced to Maerz and Paul Dictionary of Color—are as follows:

Tree:
- *Size.*—Large.
- *Vigor.*—Vigorous.
- *Growth.*—Spreading.
- *Density.*—Open.
- *Form.*—Round-topped.
- *Hardiness.*—Hardy.
- *Production.*—Productive.
- *Bearing.*—Regular bearer.

Trunk
- *Size.*—Stocky.
- *Texture.*—smooth.

Branches:
- *Size.*—Stocky.
- *Texture.*—Smooth.
- *Color.*—Green to brown.
- *Lenticels.*—Number—medium to few.

Leaves:
- *Size.*—Large. Average length—7¾". Average width—1½".
- *Form.*—Lanceolate; acutely pointed.
- *Thickness.*—Medium.
- *Texture.*—Smooth.
- *Margin.*—Serrate.
- *Petiole.*—Medium length.
- *Glands.*—Average number and position—2 to 4 on base of blade. Alternate; medium size; globose; red.
- *Stipules.*—Medium.
- *Color.*—Top side—Medium Green (23–L–9). Under side—Lighter Green (22–L–7).

Flower Buds:
- *Hardiness.*—Hardy.
- *Size.*—Large.
- *Length.*—Long.
- *Form.*—Plump; free.

Flowers:
- *Blooming period.*—About March 20th in normal year. Medium, as compared with other varieties.
- *Size.*—Large.
- *Color.*—Pink.

Fruit:
- *Maturity when described.*—Hard ripe.
- *Date of picking in normal year.*—About September 7th.
- *Size.*—Variable; large. Average diameter axially—2¾"–3". Average transversely in suture plane—2½".
- *Forms.*—Variable. Globose—slightly compressed axially.
- *Suture.*—Distinct; shallow.
- *Ventral surface.*—Rounded slightly.
- *Cavity.*—Depth—½".
- *Base.*—Rounded.
- *Apex.*—Depressed.
- *Pistil point.*—Lacking.

Skin:
- *Thickness.*—Thin.
- *Tenacity.*—Tenacious to flesh.
- *Down.*—Moderate; does not roll up when rubbed.
- *Color.*—Yellow (9–L–5) overspread to substantial extent with red (6–L–6) at maturity; the red being partly mottled and streaked.

Flesh:
- *Texture.*—Firm; fine; crisp; meaty.
- *Flavor.*—Mild.
- *Aroma.*—Pronounced.
- *Eating quality.*—Best.
- *Color.*—Yellow (10–L–6). Surface of pit cavity—Red (5–K–6) streaked lightly into flesh.

Stone:
- *Type.*—Free.
- *Size.*—Large to medium. Length—1¼". Breadth—1". Thickness—¾".
- *Apex.*—Rounded.
- *Ventral edge.*—Thin.
- *Dorsal edge.*—Narrow.
- *Ridges.*—Interrupted.
- *Color.*—Brown (8–L–7).

Use: Dessert; culinary; canning.
Keeping quality: Good.
Shipping quality: Good.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, which is large in size, hardy and vigorous in growth, spreading and round-topped in form, and a regular and productive bearer of large, late ripening freestone fruit having yellow flesh, and yellow skin substantially overspread with red at maturity; the variety being particularly characterized by the late ripening fruit whose flesh is firm, and which fruit ripens shortly before the Kirkman Gem peach.

No references cited.

ROBERT E. BAGWILL, *Primary Examiner.*